United States Patent
Anderson et al.

(10) Patent No.: US 10,617,410 B2
(45) Date of Patent: Apr. 14, 2020

(54) SUTURING DEVICE HAVING NEEDLE CAPTURE CAPABILITIES

(71) Applicant: Dura Tap LLC, Wayne, PA (US)

(72) Inventors: David Greg Anderson, Villanova, PA (US); Mark F. Kurd, Wayne, PA (US); Jay Tapper, Wayne, PA (US); Jens Johnson, Austin, TX (US)

(73) Assignee: Durastat LLC, Wayne, PA (US)

( * ) Notice: Subject to any disclaimer, the term of this patent is extended or adjusted under 35 U.S.C. 154(b) by 256 days.

(21) Appl. No.: 15/861,775

(22) Filed: Jan. 4, 2018

(65) Prior Publication Data

US 2019/0200975 A1 Jul. 4, 2019

(51) Int. Cl.
*A61B 17/04* (2006.01)
*A61B 17/062* (2006.01)
*A61B 17/06* (2006.01)

(52) U.S. Cl.
CPC ...... *A61B 17/0469* (2013.01); *A61B 17/0625* (2013.01); *A61B 17/0482* (2013.01); *A61B 17/06061* (2013.01); *A61B 2017/0608* (2013.01); *A61B 2017/06052* (2013.01)

(58) Field of Classification Search
CPC ............ A61B 17/0469; A61B 17/0482; A61B 17/0483; A61B 17/0485; A61B 17/06052; A61B 17/062; A61B 17/0625; A61B 2017/2926; A61B 2017/2927; A61B 2017/2932; A61B 2017/2933
See application file for complete search history.

(56) References Cited

U.S. PATENT DOCUMENTS

| 5,454,823 A | * | 10/1995 | Richardson | ........ | A61B 17/0469 606/145 |
| 2009/0012538 A1 | * | 1/2009 | Saliman | ............ | A61B 17/0491 606/145 |
| 2014/0316443 A1 | * | 10/2014 | Fanton | ............... | A61B 17/0469 606/145 |

* cited by examiner

*Primary Examiner* — Robert A Lynch
(74) *Attorney, Agent, or Firm* — Rankin, Hill & Clark LLP

(57) ABSTRACT

A suturing device includes an elongate body, a needle holder, a needle actuator mechanism, and a needle capture mechanism. The needle holder extends away from or is provided as part of a distal end portion of the elongate body. The needle holder defines a needle passage and a distal opening. The needle actuator interacts with a needle to move the needle from a retracted position toward the distal opening. The needle capture mechanism includes a needle capture member having a needle receiving portion. The needle receiving portion is capable of being positioned adjacent to and aligned with the distal opening in the needle holder to receive the associated needle exiting the needle passage through the distal opening and the needle receiving portion is capable of being offset from the distal opening so as to receive tissue between the needle capture member and the needle holder.

17 Claims, 6 Drawing Sheets

SUTURING DEVICE HAVING NEEDLE CAPTURE CAPABILITIES

BACKGROUND

The present disclosure relates generally to surgery and the placement of the sutures.

Surgical closure using sutures is one approach to tissue repair. In some instances, however, placing sutures can be difficult to execute due to anatomic constraints, obstruction of visualization by blood or other bodily fluids, and the proximity to nerve rootlets. These challenges can be further complicated when using minimally invasive techniques, for example when working through a tubular retractor.

Known needle drivers, which are often used when suturing in challenging locations, lack a mechanism for capturing a needle once it has been passed through tissue to be sutured.

SUMMARY

In view of the foregoing, a suturing device includes an elongate body, a needle holder, a needle actuator mechanism, and a needle capture mechanism. The elongate body includes a proximal end portion and a distal end portion. The needle holder extends away from the distal end portion or is provided as part of the distal end portion of the elongate body. The needle holder defines a needle passage and a distal opening. The needle actuator is configured to move an associated needle in an advance direction with respect to the needle holder from a retracted position toward the distal opening. The needle capture mechanism includes a needle capture member having a needle receiving portion. The needle capture member is connected with at least one of the elongate body and the needle holder. The needle capture member is moveable with respect to the needle holder such that that needle receiving portion is capable of being positioned adjacent to and aligned with the distal opening in the needle holder to receive the associated needle exiting the needle passage through the distal opening and the needle receiving portion is capable of being offset from the distal opening to receive tissue between the needle capture member and the needle holder.

Another example of a suturing device includes a needle, a suture, an elongate body, a needle holder, a needle actuator mechanism, and a needle capture mechanism. The needle has a first end, which is pointed, and a second end. The suture connects with the needle. The elongate body includes a proximal end portion and a distal end portion. The needle holder extends away from the distal end portion or is provided as part of the distal end portion of the elongate body. The needle holder defines a needle passage and a distal opening. The needle actuator mechanism interacts with the needle to move the needle with respect to the needle holder from a retracted position in an advance direction toward the distal opening, the retracted position being a position in which the first end of the needle is positioned within the needle passage. The needle capture mechanism includes a needle capture member having a needle receiving portion. The needle capture member is connected with at least one of the elongate body and the needle holder. The needle capture member is movable with respect to the needle holder such that the needle receiving portion is capable of being positioned adjacent to and aligned with the distal opening in the needle holder so as to receive the needle exiting the needle passage through the distal opening and the needle receiving portion is also capable of being offset from the distal opening so as to receive tissue between the needle capture member and the needle holder.

DETAILED DESCRIPTION

Figure 1:
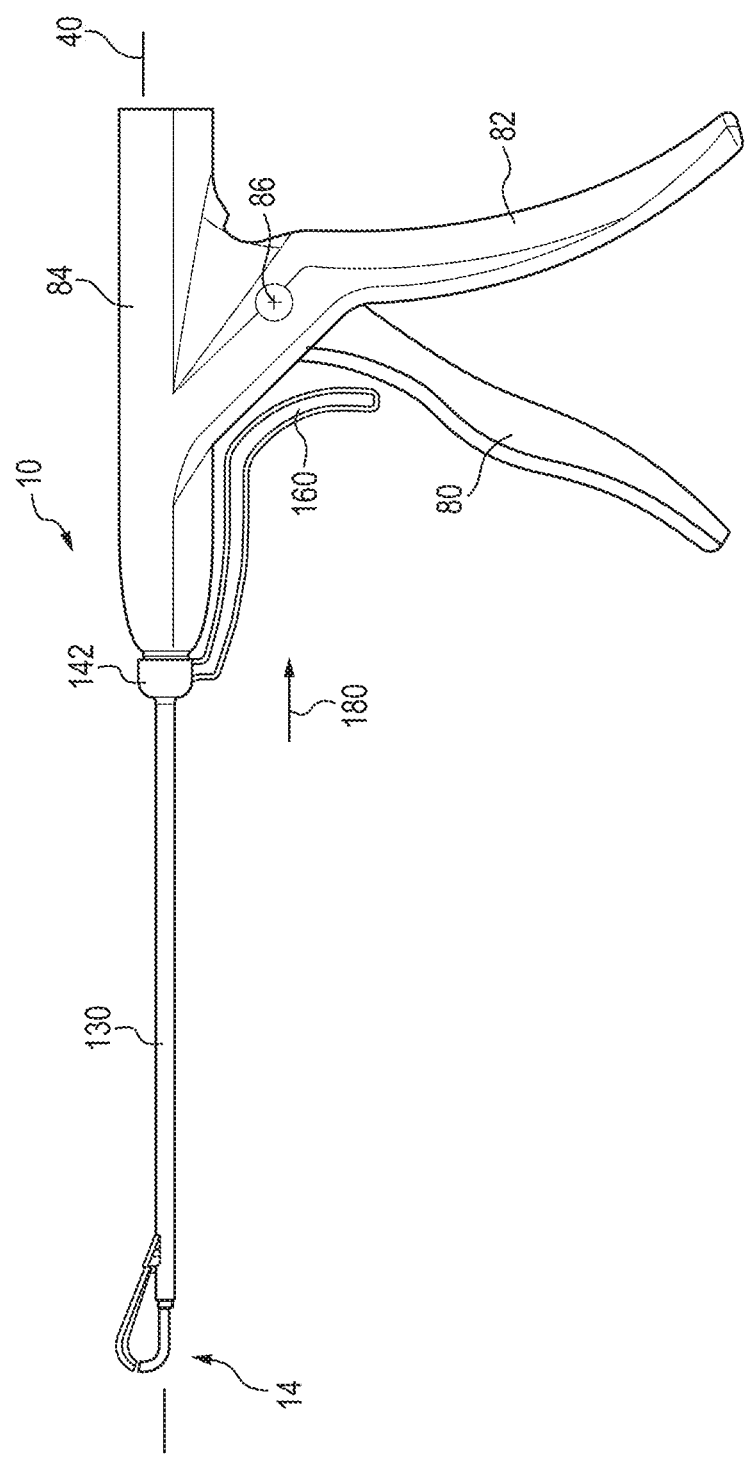
FIG. 1 is a side view of a suturing device.
Figure 2:
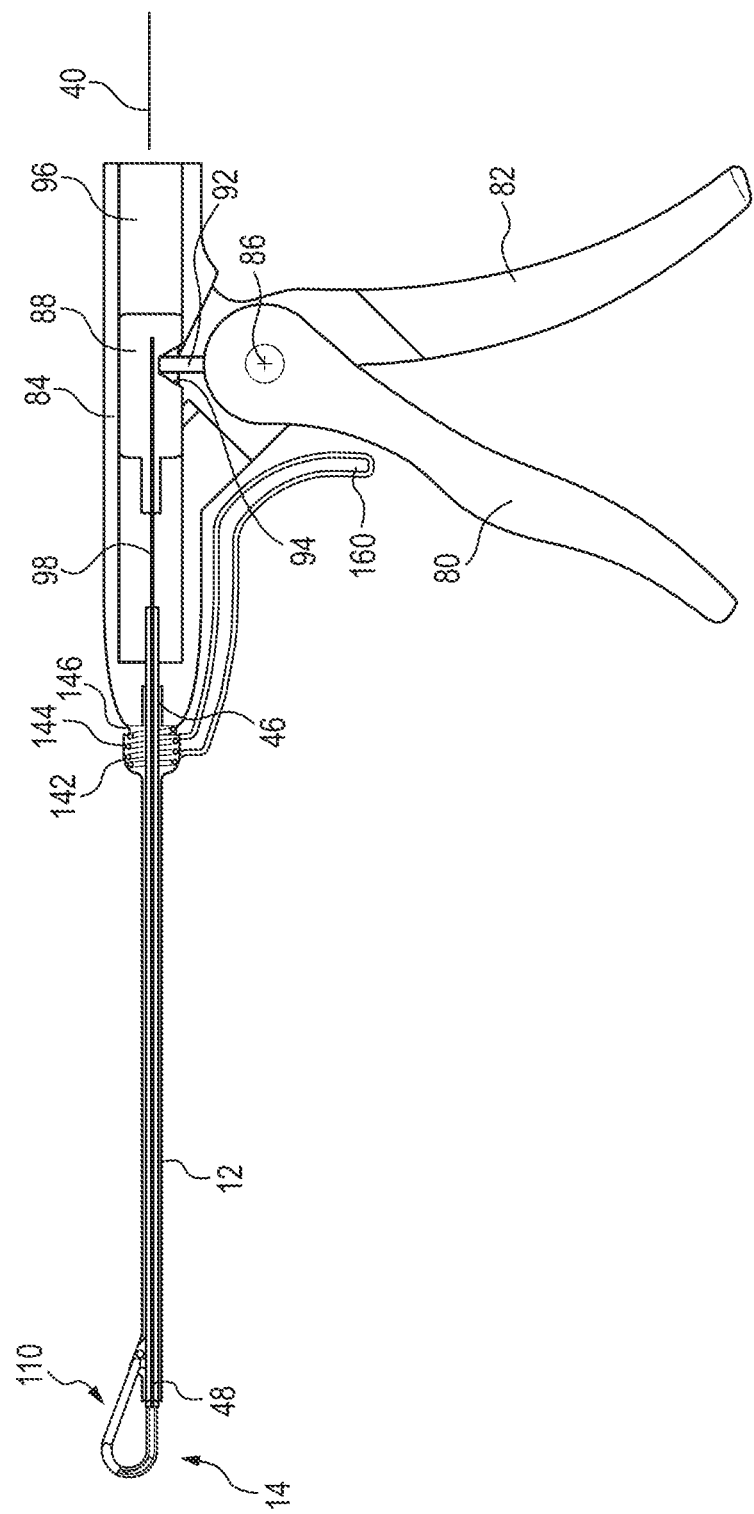
FIG. 2 is a cross-sectional view of the suturing device depicted in FIG. 1.
Figure 3:
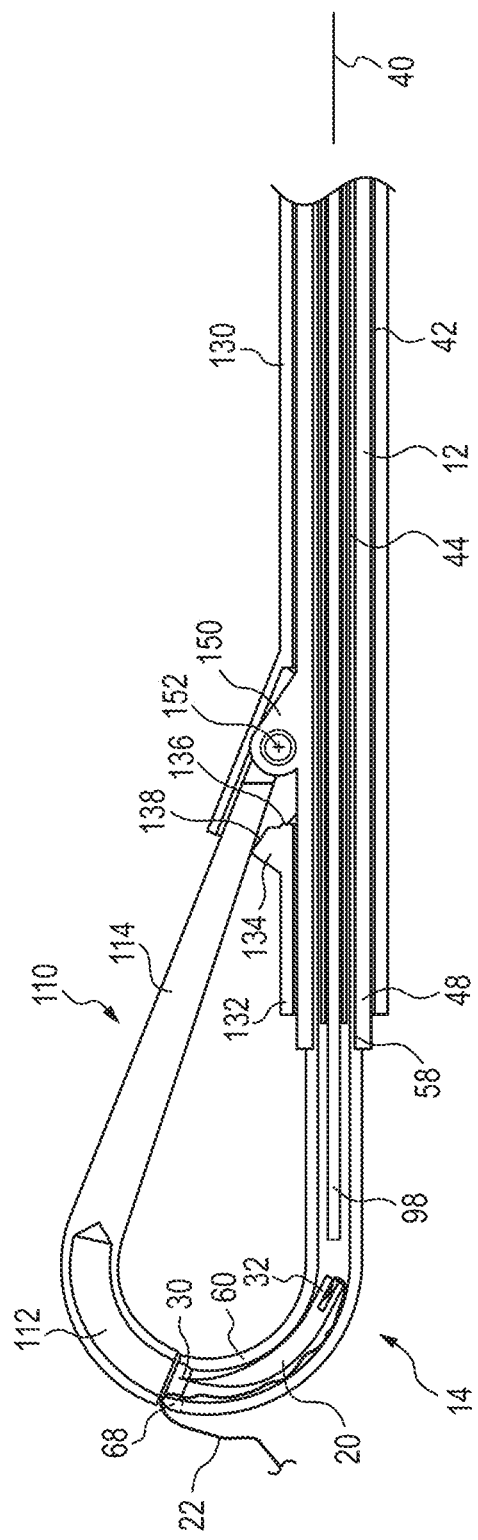
FIGS. 3-6 are cross-sectional views of a distal end portion of the suturing device of FIG. 1 with a needle capture mechanism in different operating positions.
Figure 4:
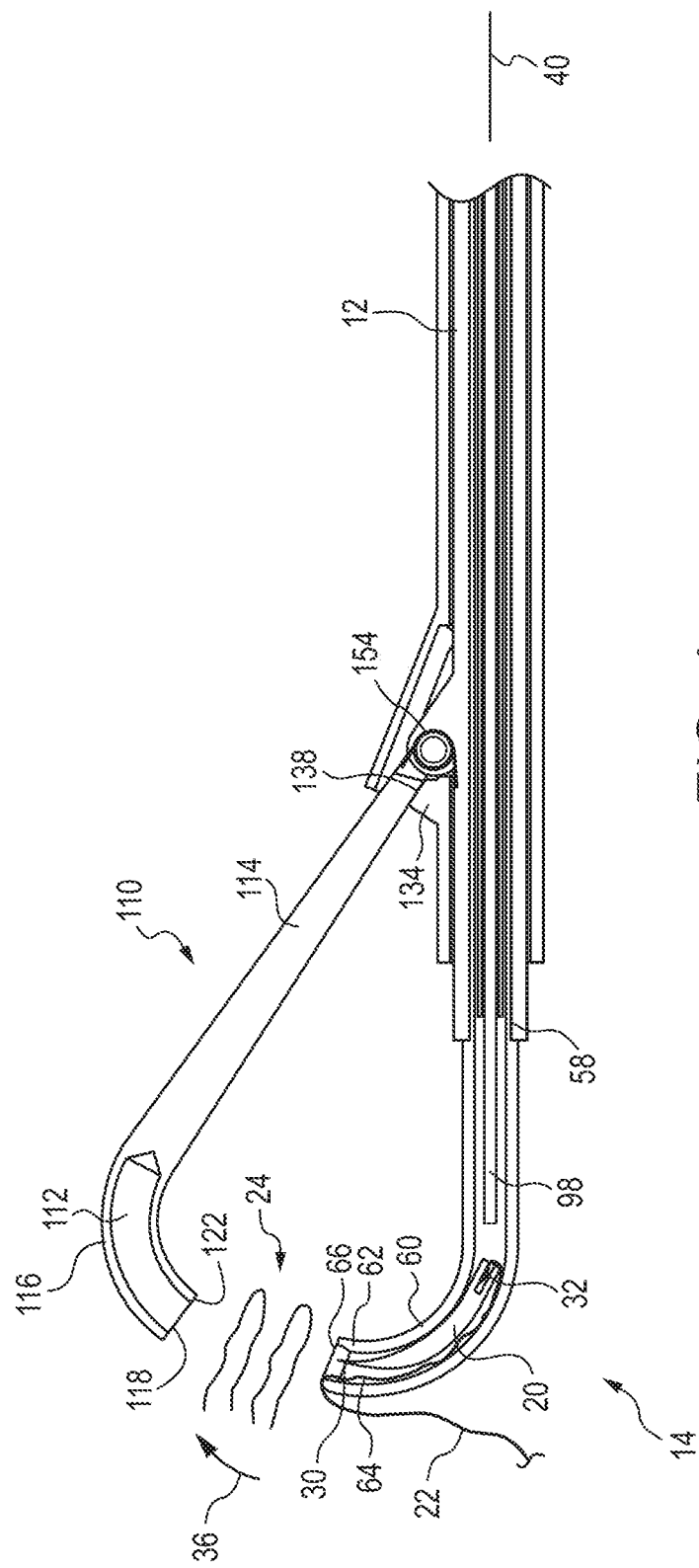

FIG. 1 depicts an example of a suturing device 10 that is useful to suture tissue that can be used in many different types of surgical procedures. The descriptions and drawings herein are merely illustrative and various modifications and changes can be made in the structures disclosed without departing from the scope of the appended claims. With reference to FIGS. 1 and 2, the suturing device 10 includes an elongate body 12, a needle holder 14, a needle actuator mechanism, and a needle capture mechanism. The suturing device 10 is particularly useful during a minimally invasive surgical procedure performed through a tubular retractor or other small surgical portal; however, the suturing device 10 can be used elsewhere. With reference to FIGS. 3 and 4, the suturing device 10 accurately locates a needle 20 and a suture 22 with respect to target tissue 24 to be sutured.

With reference to FIG. 3, the needle 20 in the illustrated embodiment is a curved needle having a first end 30, which is pointed, and a second end 32, which is opposite to the first end 30. The needle 20 can be made similar to commercially available curved needles made from known materials. The needle 20 can take other configurations, such as straight, and could be formed as part of the suture 22, e.g., the needle could be a rigid end of the suture 22 that is configured so as to be suitable to pass through the tissue 24. Actuation of the needle actuator mechanism (described below) moves the needle 20 in an advance direction 36 (FIG. 4) with respect to the needle holder 16. The needle 20 moves from a retracted position, which is shown in FIG. 3 where the pointed end 30 of the needle 20 is positioned within the needle holder 14, through the target tissue 24 in a manner that will be described in more detail below.

The suture 22 connects with the needle 20 and extends from the second end 32 of the needle 20 in the illustrated embodiment. The suture 22 can be swaged to the second end 32 of the needle 20. The suture 22 can also connect with the needle 20 in other conventional manners. The suture 22 can be acquired from known suture manufacturers. The average diameter of the suture 22 can be very close to the outer diameter of the second end 32 of needle 20, for example, the average diameter of the suture 22 can be between 90% and 110% of the diameter of the second end of the needle 20.

The elongate body 12 in the illustrated embodiment is in the form of a cannula and extends along a longitudinal axis 40. With respect to FIG. 3, the elongate body 12 has an outer surface 42, which is smooth, and defines a track 44, which is a lumen in the illustrated embodiment. The elongate body 12 can take other configurations, for example the track 44 may not be circular in a cross section taken normal to the longitudinal axis 40, but instead could be U-shaped. In the illustrated embodiment, the elongate body 12 is circular in a cross section taken normal to the longitudinal axis 40; however, the elongate body 12 could take alternative configurations, such as polygonal or U-shaped in cross section.

The elongate body 12 includes a proximal end portion 46 (FIG. 2) and a distal end portion 48. In the illustrated embodiment, the needle holder 14 is received in and connected with the elongate body 12 and extends away from the distal end portion 48 of the elongate body 12. In the illustrated embodiment, the elongate body 12 is made from metal and extends along the longitudinal axis 40. In the illustrated embodiment, an outer diameter of the elongate body 12 is constant between the proximal end portion 46 and the distal end portion 48. The outer diameter can be less than 3.5 mm, which provides a very slim device to enhance the line of sight for a surgeon during a surgical procedure.

The needle holder 14 extends away from the distal end portion 48 or is provided as part of the distal end portion 48 of the elongate body 12. The needle holder 14 is a hollow tubular member in the illustrated embodiment. A proximal end section 58 of the needle holder 14 that is coaxial with the longitudinal axis 40 is received inside the elongate body 12; however, the needle holder 14 could be formed as part of the elongate body, e.g., both the elongate body 12 and the needle holder 14 could be made from one tubular stock material. In an alternative arrangement, the elongate body 12 and the needle holder 14 can be formed from elongate generally U-shaped in cross section material that are connected in a clam-shell type configuration. The needle holder 14 depicted in the illustrated embodiment is a curved needle holder having a curved section 60 that generally follows a constant radius such that the suturing device 10 can have a J-hook configuration at a distal end thereof. The needle holder 14 includes a distal-most tip 62 and defines a needle passage 64 that is in communication with the track 44. The needle passage 64 terminates at a distal opening 66 that is offset from the longitudinal axis 40. The needle holder 14 can also be provided with a notch 68 (depicted in only FIG. 3) near the distal most tip 62. The suture 22 can be received in the notch 68 when the needle is in the retracted position shown in FIG. 3. The notch 68 can facilitate deployment of the needle 20 from the suturing device 10 and mitigate the likelihood that the pointed end 30 of the needle 20 pierces the suture 22 during deployment.

The needle actuator mechanism is configured to interact with the needle 20 to move the needle 20 in the advance direction 36 with respect to the needle holder 14 from the retracted position (shown in FIG. 3) toward the distal opening 66. As seen in FIGS. 3 and 4, the needle 20 is in the retracted position when the pointed end 30 of the needle 20 is positioned within the needle passage 64 of the needle holder 14. The needle actuator mechanism includes a manually operated actuator, which in the illustrated embodiment is a needle trigger 80 (FIGS. 1 and 2) that is moveable with respect to a fixed handle 82 extending from a proximal housing 84. The needle trigger 80 is just one example of a manually operated actuator. Moreover, the needle actuator mechanism could include other movable actuators that could be operated by a robot, for example.

With reference back to the illustrated embodiment, the needle trigger 80 connects with the fixed handle 82 and the proximal housing 84 so as to be rotatable with respect to the fixed handle 82 about a needle trigger pivot axis 86. The needle trigger 80 is operatively connected with a slider 88 such that movement of the needle trigger 80 results in movement of the slider 88. More particularly, pivotal movement of the needle trigger 80 toward the fixed handle 82 about the needle trigger pivot axis 86 results in translational movement of the slider 88 along the longitudinal axis 40. With respect to FIG. 2, an arm 92 extends from the needle trigger 80 and is received in a recess 94 of the slider 88 to operatively connect the needle trigger 80 with the slider 88. The slider 88 is positioned within a cavity 96 provided in the proximal housing 84. The slider 88 connects with a wire 98, which in the illustrated embodiment is made of Nitinol. The wire 98 extends through the track 44 of the elongate body 12 and into the needle passage 64 of the needle holder 14 when the needle trigger 80 is squeezed to rotate the needle trigger 80 with respect to the fixed handle 82.

The needle capture mechanism includes a needle capture member 110 having a needle receiving portion 112. As more clearly seen in FIG. 6, the needle capture member 110 is configured to receive the needle 20 and enclose the pointed end 30 of the needle 20 after the needle 20 has exited the needle passage 64. This allows for removal of a distal end of the suturing device 10 from the area where the suture 22 has been passed through the tissue 24 and reduces the likelihood of any possible snagging of tissue when removing the suturing device 10. The needle capture member 110 is connected with at least one of the elongate body 12 and the needle holder 14, and in the illustrated embodiment, extends from the elongate body 12. The needle capture member 110 is movable with respect to the needle holder 14 such that the needle receiving portion 112 is capable of being positioned adjacent to and aligned with the distal opening 66 in the needle holder 14 so as to receive the needle 20 exiting the needle passage 64 through the distal opening 66 (see FIG. 5). The needle capture member 110 is also movable such that the needle receiving portion 112 is capable of being offset from the distal opening 66 of the needle holder 14 so that tissue 24 can be received between the needle capture member 110 and the needle holder 14 which is shown in FIG. 4.

The needle capture member 110 includes a straight section 114 and a curved section 116 to take an overall J-hook configuration. The curved section 116 defines a needle receiving passage, which in the illustrated embodiment is the needle receiving portion 112 of the needle capture member 110. The needle receiving passage terminates at a distal aperture 118 at a distal end 122 of the needle capture member 110. The distal aperture 118 aligns with the distal opening 66 in the needle holder 14 when the needle capture member 110 is brought towards and adjacent to the needle holder 14. The distal end 122 of the needle capture member 110 can contact the distal-most tip 62 of the needle holder 14 and at least substantially cover the distal opening 66 when in contact with the distal-most tip 62. In the illustrated embodiment, the curved section 116 has a maximum outer diameter between 90% and 110% of a maximum outer diameter of the needle holder 14 adjacent the distal opening 66. Also, the curved section 60 of the needle holder 14 and the curved section 116 of the needle capture member 110 substantially follow the same radius.

The needle capture mechanism also includes a needle capture sleeve 130 that at least partially surrounds the elongate body 12. The needle capture sleeve 130 includes a distal end 132 adjacent to the needle holder 14. A bump 134 is provided on the needle capture sleeve 130 adjacent to the distal end 132. The bump 134 is provided on a distal side of a needle capture member mount opening 136 provided in the needle capture sleeve 130. The bump 134 defines a movable inclined surface 138 that is movable with respect to the needle capture member 110. The movable inclined surface 138 contacts the needle capture member 110 to move the needle capture member 110 away from the distal opening 66 in the needle holder 14, which can be seen when comparing FIG. 3 to FIG. 4. The movable inclined surface 138 is provided on the needle capture sleeve 130, which is movable with respect to the elongate body 12.

With reference back to FIGS. 1 and 2, the needle capture sleeve 130 also includes a spring shroud 142 at a proximal end. The spring shroud 142 covers a spring 144 that acts against a distal end surface 146 of the proximal housing 84 to bias the needle capture sleeve 130 toward the needle holder 14 along the longitudinal axis 40. Accordingly, the movable inclined surface 138 on the needle capture sleeve 130 is biased toward the needle holder 14 such that the needle capture member 110 is normally in the position depicted in FIG. 3.

A needle capture member mount 150, which extends from the elongate body 12 in the illustrated embodiment, extends through the needle capture member mount opening 136 provided in the needle capture sleeve 130. The needle capture member 110 connects with the needle capture member mount 150 so as to pivot with respect to the elongate body 12 and the needle holder 14 about a needle capture member axis 152. A needle capture biasing spring 154 (only schematically depicted in FIG. 4) biases the distal end 122 of the needle capture member 110 towards the distal opening 66 of the needle holder 14.

The needle capture mechanism also includes a needle capture actuator that is manually operated and operatively connected with the needle capture member 110. With reference back to FIG. 1, the needle capture actuator in the illustrated embodiment is a needle capture trigger 160 that is connected with the needle capture sleeve 130 through the spring shroud 142. The needle capture trigger 160 is movable with respect to the proximal housing 84 to compress the spring 144 in the spring shroud 142. The needle capture trigger 160 translates in an axis parallel with the longitudinal axis 40.

Figure 5:
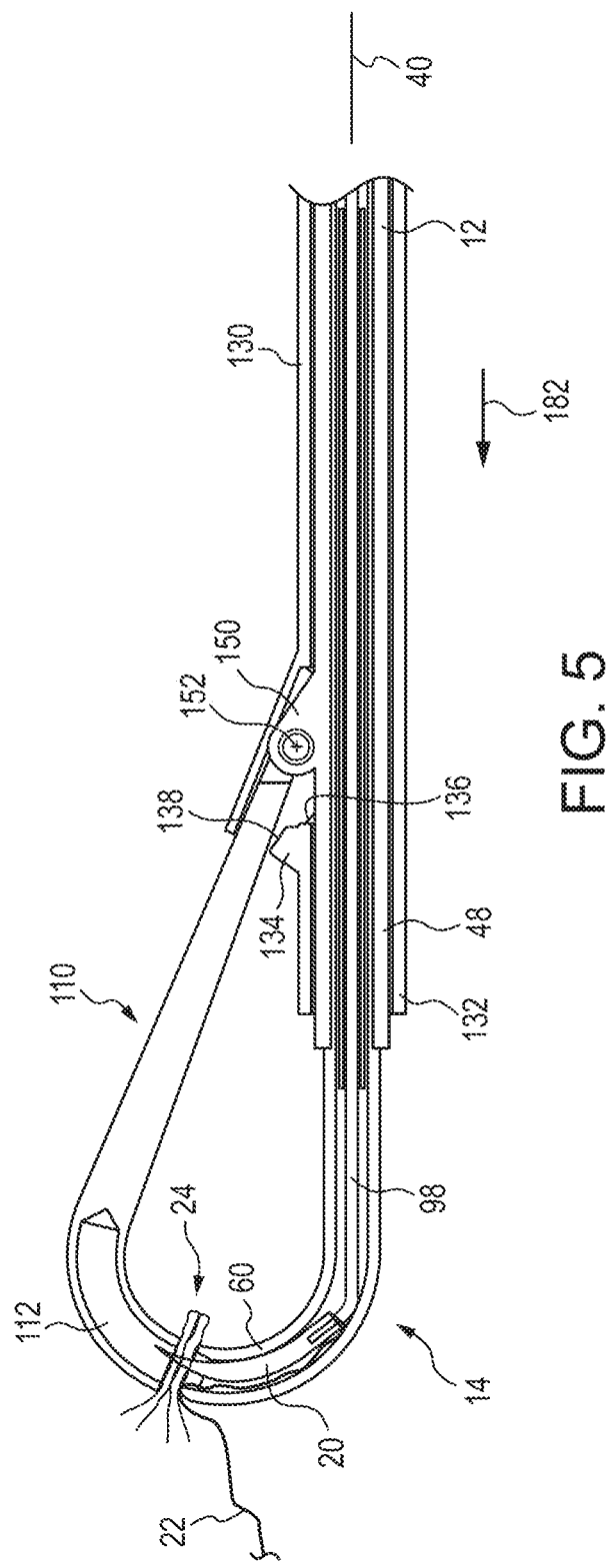

In use, the suturing device 10 is placed in an area of interest with the needle capture member 110 in the position shown in FIG. 3. An operator squeezes the needle capture trigger 160 moving the needle capture trigger 160 in the direction of arrow 180, which moves the needle capture sleeve 130 also in the direction of the arrow 180. The movable inclined surface 138 contacts the needle capture member 110, which moves the distal aperture 118 of the needle capture member 110 away from the distal opening 66 of the needle holder 14 as shown in FIG. 4. Tissue 24 to be sutured can be received between the needle holder 14 and the needle capture member 110. The surgeon then releases the needle capture trigger 160 and the spring 144 biases the needle capture sleeve 130 in the direction of arrow 182 (FIG. 5), which is opposite to the direction of the arrow 180. Accordingly, the movable inclined surface 138 moves away from the needle capture member 110 and the needle capture biasing spring 154 biases the needle capture member 110 so that the distal aperture 118 of the needle capture member 110 is positioned adjacent to and aligned with the distal opening 66 of the needle holder 14, which is shown in FIG. 5. As such, the tissue 24 is trapped between the needle capture member 110 and the needle holder 14.

Figure 6:
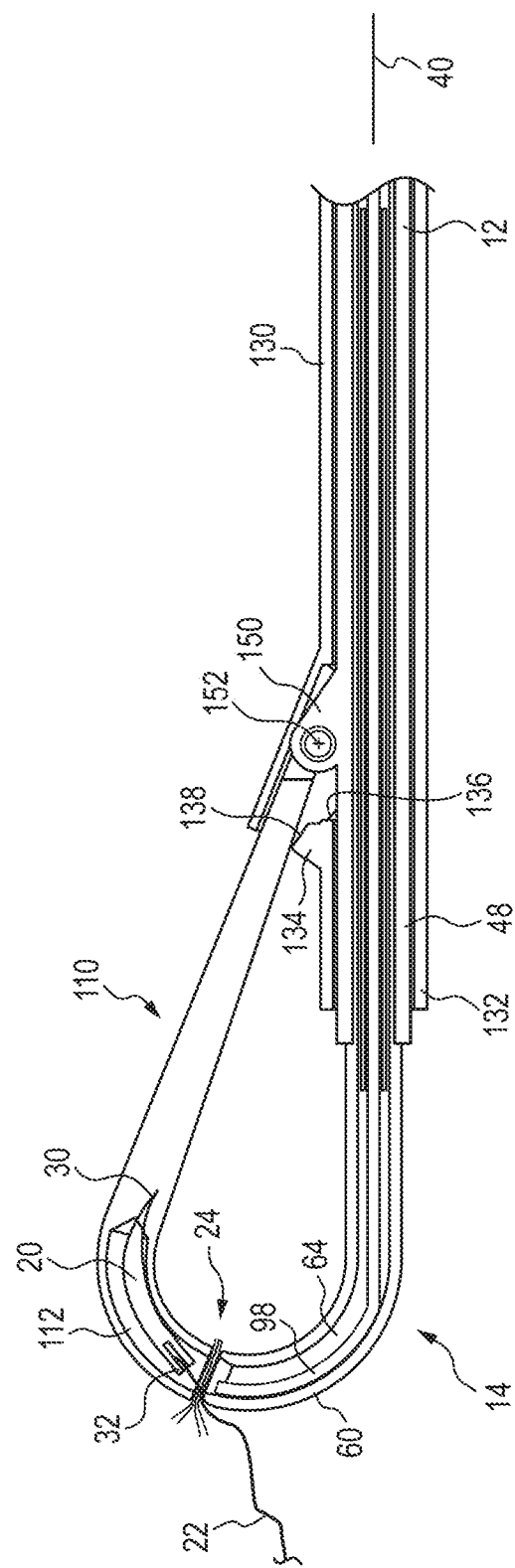

The surgeon can then squeeze the needle trigger 80 to rotate the needle trigger 80 about the needle trigger pivot axis 86 with respect to the fixed handle 82 and the proximal housing 84. This moves the slider 88 in the direction of the arrow 182 so that the wire 98 contacts the needle 20 to move the needle in the advance direction 36 through the tissue 24. With reference to FIG. 6, the needle continues to move in the advance direction 36 to be received in the needle receiving portion 112 in the needle capture member 110. The needle receiving portion 112 can be configured to catch the needle 20 and preclude removal of the needle 20 when the needle capture member 110 is moved away from the needle holder 14 with the needle 20 received in the needle receiving portion 112. After the needle 20 has passed through the tissue 24 and is caught inside the needle receiving portion 112, the surgeon can then squeeze the needle capture trigger 160 moving the needle capture trigger 160 in the direction of arrow 180 to release the tissue 24. After the tissue 24 has been released, the needle capture trigger 160 can be released and the spring 144 biases the needle capture sleeve 130 in the direction of arrow 182. The needle capture biasing spring 154 also biases the needle capture member 110 back towards the needle holder 14 to cover the distal opening 66. Then, the surgeon can remove the distal end of the suturing device 10 from the area of interest.

A suturing device and a method using the suturing device has been described above with particularity. Modifications and alterations will occur to those upon reading and understanding the detailed description. The invention, however, is not limited to only the embodiments described above. Instead, the invention is broadly defined by the appended claims and the equivalents thereof.

The invention claimed is:

1. A suturing device comprising:
   a needle having a first end, which is pointed, and a second end;
   a suture connected with the needle;
   an elongate body including a proximal end portion and a distal end portion;
   a needle holder extending away from the distal end portion or provided as part of the distal end portion of the elongate body, the needle holder defining a needle passage and a distal opening;
   a needle actuator mechanism interacting with the needle to move the needle with respect to the needle holder from a retracted position in which the first end of the needle is positioned within the needle passage in an advance direction toward the distal opening; and
   a needle capture member including a needle receiving portion, the needle capture member being connected with at least one of the elongate body and the needle holder and movable with respect to the needle holder such that the needle receiving portion is capable of being positioned adjacent to and aligned with the distal opening in the needle holder so as to receive the needle exiting the needle passage through the distal opening and the needle receiving portion is capable of being offset from the distal opening,
   wherein at least a portion of the suture extends along the needle passage toward the distal opening between the needle and an inner surface of the needle holder when the needle is received in the needle passage in the retracted position.

2. The suturing device of claim 1, wherein the needle capture member is configured to receive the needle and enclose the first end of the needle after the needle as exited the needle passage.

3. The suturing device of claim 1, wherein the needle passage is curved.

4. The suturing device of claim 1, wherein the needle capture member pivots with respect to the needle holder.

5. The suturing device of claim 4, further comprising a movable inclined surface that is movable with respect to the needle capture member, wherein the movable inclined surface contacts the needle capture member to move the needle receiving portion of the needle capture member away from the distal opening.

6. The suturing device of claim 5, further comprising a needle capture sleeve at least partially surrounding the elongate body, and the movable inclined surface is provided on the needle capture sleeve, which is movable with respect to the elongate body.

7. The suturing device of claim 1, further comprising a needle capture biasing spring biasing a distal end of the needle capture member towards the distal opening.

8. The suturing device of claim 1, wherein the needle capture member includes a curved section having a maximum outer diameter between 90% and 110% of a maximum outer diameter of the needle holder adjacent the distal opening.

9. The suturing device of claim 8, wherein the needle holder includes a curved section and the curved section of the needle capture member and the curved section of the needle holder substantially follow the same radius.

10. The suturing device of claim 1, wherein the needle capture member includes a curved section defining a needle receiving passage, which is the needle receiving portion of the needle capture member.

11. The suturing device of claim 10, wherein the needle capture member includes a distal aperture which leads to the needle receiving passage.

12. The suturing device of claim 1, further comprising a needle capture actuator that is manually operated and operatively connected with the needle capture member.

13. The suturing device of claim 12, wherein the needle capture actuator is a needle capture trigger.

14. The suturing device of claim 13, wherein the needle actuator mechanism includes a needle trigger.

15. The suturing device of claim 14, wherein the needle capture trigger translates and the needle trigger pivots.

16. The suturing device of claim 1, wherein at least a portion of the suture extends through the distal opening when the needle is received in the needle passage in the retracted position.

17. The suturing device of claim 1, wherein the needle capture member is configured to receive the needle and enclose the first end of the needle after the needle has exited the needle passage, wherein the needle capture member includes a curved section having a maximum outer diameter between 90% and 110% of a maximum outer diameter of the needle holder adjacent the distal opening, wherein the needle holder also includes a curved section and the curved section of the needle capture member and the curved section of the needle holder substantially follow the same radius.

* * * * *